(12) United States Patent
Byrum et al.

(10) Patent No.: US 7,144,400 B2
(45) Date of Patent: Dec. 5, 2006

(54) GASTRIC BAND INTRODUCTION DEVICE

(75) Inventors: Randal T. Byrum, Milford, OH (US); Sean P. Conlon, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/676,288

(22) Filed: Oct. 1, 2003

(65) Prior Publication Data

US 2005/0075652 A1    Apr. 7, 2005

(51) Int. Cl.
*A61B 17/10* (2006.01)

(52) U.S. Cl. ............ 606/140; 606/151; 606/157; 128/899; 604/909

(58) Field of Classification Search ............ 606/139, 606/140, 141, 151, 157; 128/899; 604/909
See application file for complete search history.

(56) References Cited

U.S. PATENT DOCUMENTS

| 4,592,355 | A | * | 6/1986 | Antebi ............ 606/144 |
| 5,618,304 | A | * | 4/1997 | Hart et al. ......... 606/205 |
| 5,658,298 | A | * | 8/1997 | Vincent et al. ...... 606/139 |
| 6,383,197 | B1 | | 5/2002 | Conlon et al. |
| 6,409,733 | B1 | | 6/2002 | Conlon et al. |

* cited by examiner

*Primary Examiner*—Michael J. Hayes
*Assistant Examiner*—Michael G. Mendoza
(74) *Attorney, Agent, or Firm*—Dean L. Garner

(57) ABSTRACT

A surgical tool for safely introducing a gastric band into a patient's abdomen is provided. The instrument includes an inner rod slidably and coaxially disposed within a support tube. The inner rod includes a gastric band releasably secured thereon. Distal movement of the inner rod into the support tube exposes said gastric band.

20 Claims, 3 Drawing Sheets

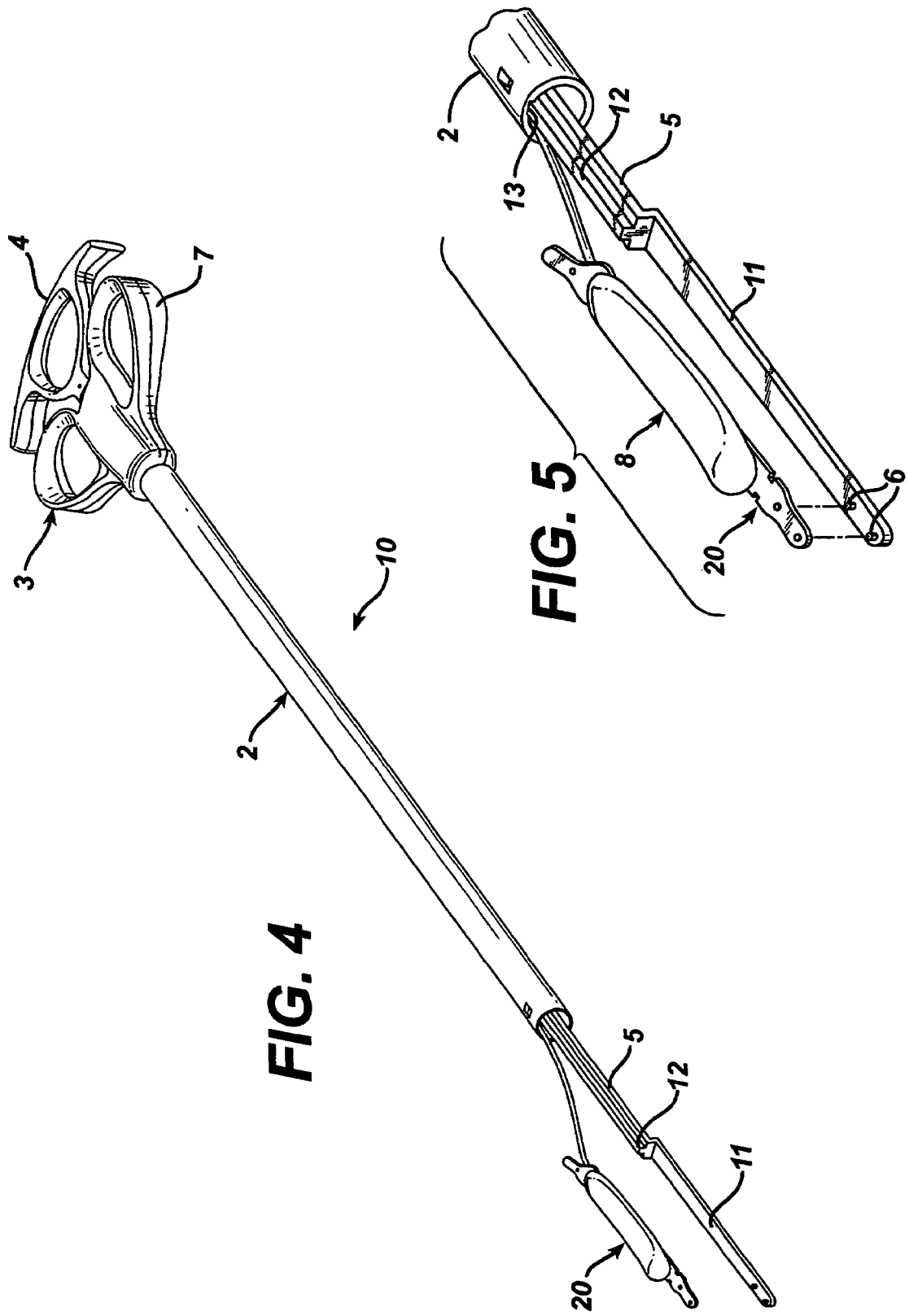

GASTRIC BAND INTRODUCTION DEVICE

BACKGROUND OF THE INVENTION

Over the years many methods of treating morbid obesity have been undertaken. One of the more promising methods employs the placement of a circumscribing band, commonly known as a "gastric band", around a portion of the stomach whereby the stomach may be compressed thereby creating a stoma opening that is smaller than the normal interior diameter of the stomach thereby restricting food intake into the lower digestive portion of the stomach.

Typically, the gastric band is introduced into a patient's abdomen by pushing it through a large trocar or trocar site by hand. This method of introduction increases the risk of infection resulting from the gastric band contacting the patient's skin. Inserting the gastric band directly through a trocar may also undesirably damage the gastric band. Consequently, a significant need exists for a surgical instrument that enables the introduction of a gastric band into a patient's abdomen without coming in direct contact with the patient's skin or trocar.

BRIEF SUMMARY OF THE INVENTION

The present invention overcomes the above noted and other deficiencies in the prior art by providing a surgical instrument that allows for the introduction of a gastric band into a patient's abdomen without allowing the gastric band to contact the patient's skin or a trocar.

In accordance with one embodiment of the invention, the surgical instrument includes an elongated inner rod within an elongated support tube. The inner rod includes a mechanism for releasably engaging a gastric band. When the inner rod is slid into the support tube, the mechanism for releasably engaging a gastric band is exposed.

In another embodiment of the invention, the surgical instrument similarly includes an elongated inner rod within an elongated support tube. The inner rod includes a releasably engaged gastric band on one end. When the inner rod is slid into the support tube, the gastric band is exposed.

The above summary of the present invention is not intended to describe each embodiment or every implementation of the present invention. Advantages and attainments, together with a more complete understanding the invention, will become apparent and appreciated by referring to the following detailed description and claims taken in conjunction with the accompanying drawings.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 is an isometric view of an actuated gastric band introduction device with the gastric band partially removed from the inner rod; and FIG. 5 is an enlarged partial view of the isometric view of FIG. 4 showing the distal end of the support tube and the distal end of the inner rod with the gastric band partially removed.

DETAILED DESCRIPTION OF THE INVENTION

Figure 1:
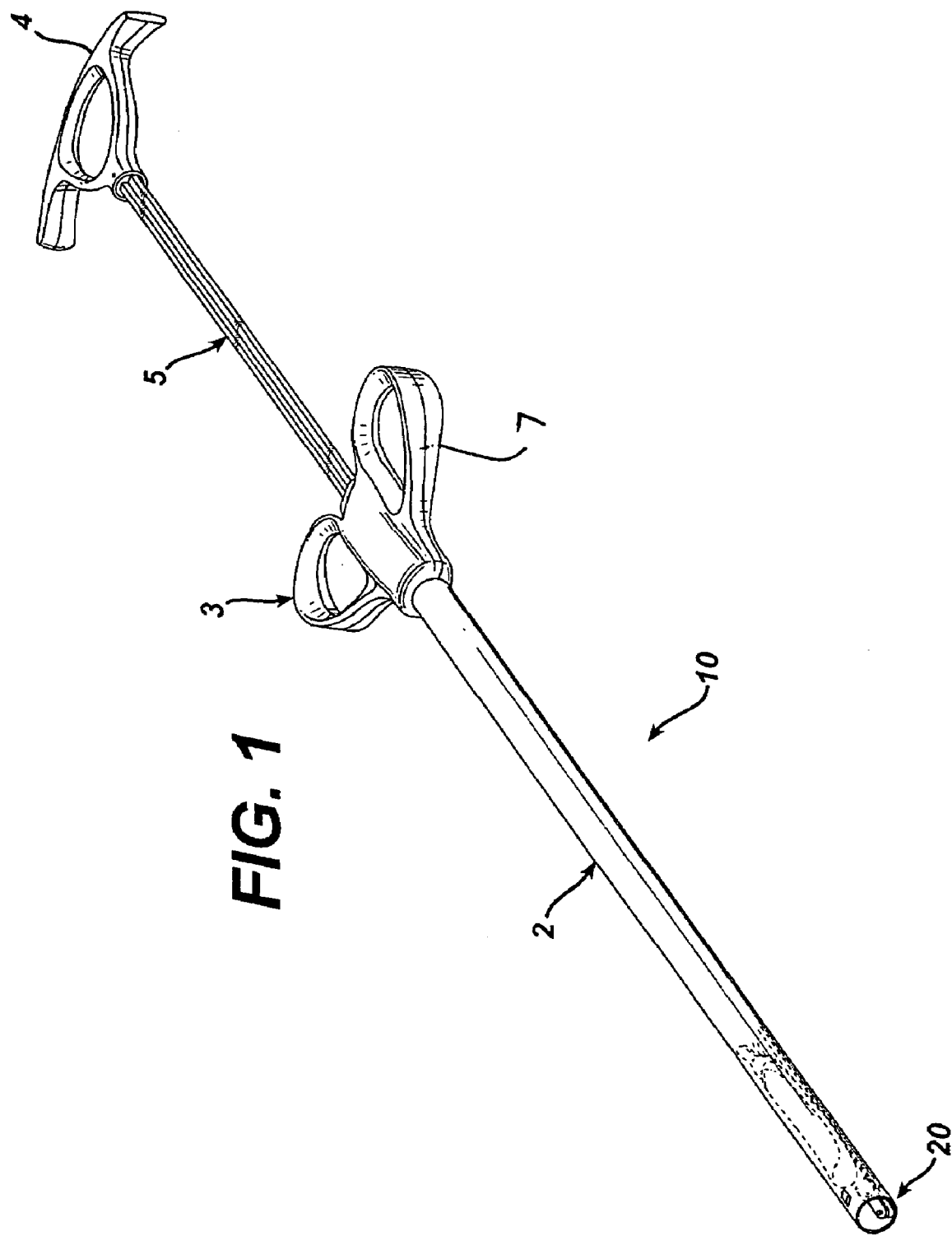
FIG. 1 is an isometric view of an unactuated gastric band introduction device.
Figure 2:
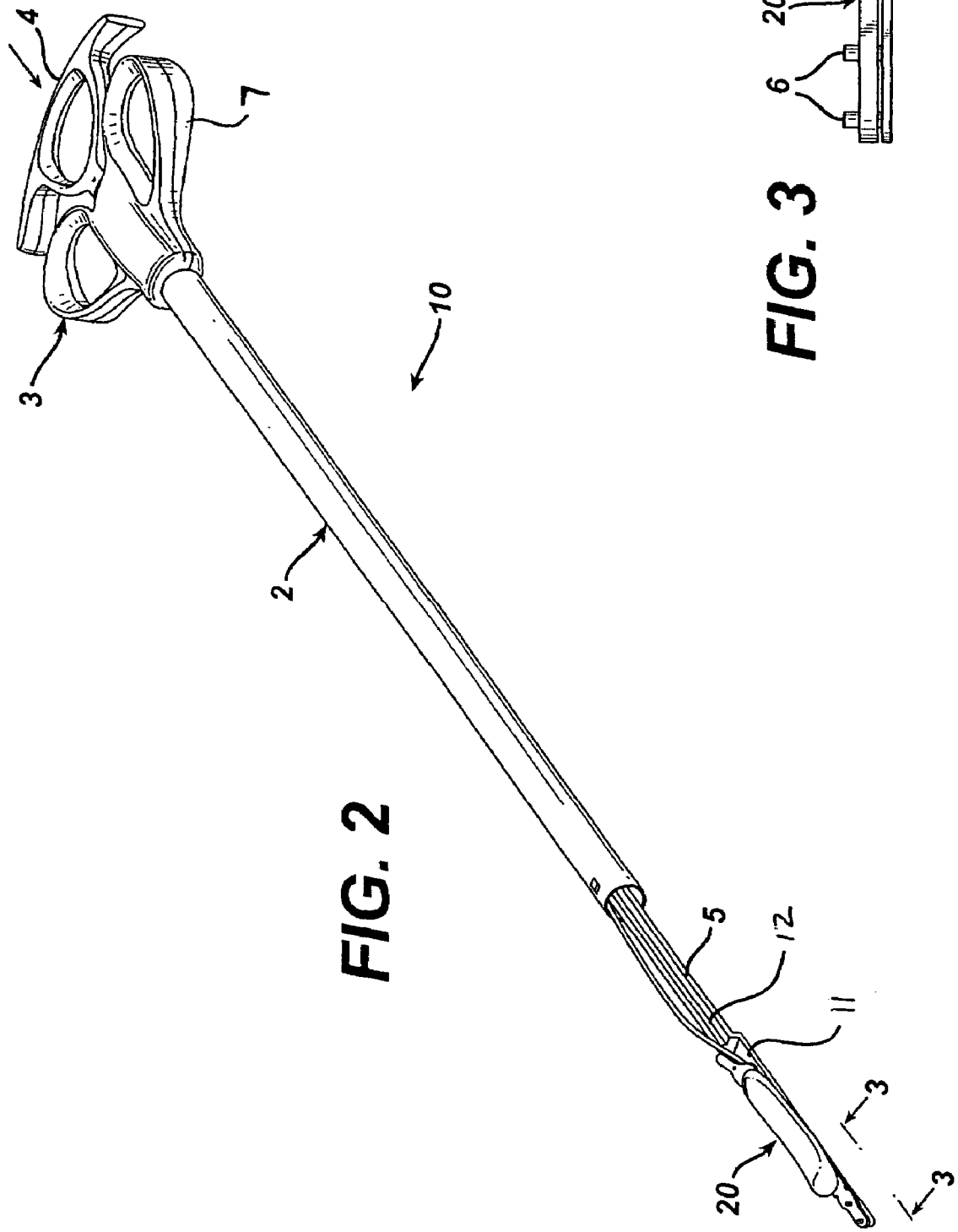
FIG. 2 is an isometric view of an actuated gastric band introduction device.
Figure 3:
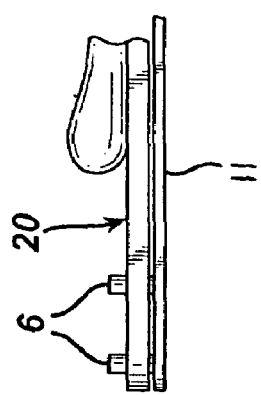
FIG. 3 is a partial side view of the distal end of the inner rod of gastric band introduction device.

Referring now to the FIGS. wherein like numerals indicate the same elements throughout the views, there is shown in FIG. 1 an isometric view of an unactuated gastric band introduction device 10 ready for introduction into a patient. The gastric band introduction device 10 includes an elongated support tube 2 with a handle 7 at a proximal end. The gastric band introduction device 10 preferably includes a pair of opposed finger loops 3 extending outwardly from the handle 7. An inner rod 5 is slidingly located within the support tube 2 and has a thumb ring 4 at a proximal end and one or more upwardly protruding pins 6 for engaging a gastric band 20 at the distal end. The inner rod 5 may also include a shelf 11 located at the distal end of the support tube 2 for holding a gastric band 20. The inner rod 5 may also include a longitudinal protrusion 12 which may engage a longitudinal groove 13 in the support tube 2 for effecting the sliding engagement between the inner rod 5 and support tube 2 and also for stabilizing the inner rod 5 when it is inserted into the support tube 5.

The support tube 2 is preferably comprised of stainless steel but may be comprised of any durable engineering plastic. Preferably, the support tube 2 has a diameter of about 10 mm to about 20 mm and more preferably between about 12 mm and about 15 mm. Preferably, the support tube 2 is between about 30 cm and about 50 cm in length and more preferably about 43 cm. However, it should be appreciated that the support tube 2 can be adapted in both length and diameter to accommodate any kind of gastric band or to fit within any sized trocar. The handle 7, the finger loops 3, the inner rod 5, and the thumb ring 4 can be comprised of either stainless steel or any suitably durable engineering plastic. While pins 6 are shown in the illustrative embodiment, any other mechanism, such as a clip or a strap, which will releasably secure the gastric band to the inner rod while also allowing the gastric band to be easily removed from the inner rod will suffice.

FIGS. 2 through 5 show the gastric band introduction device 10 after the device has been actuated to deploy a gastric band 20 from the distal end of the support tube 5. In FIGS. 2 through 5, the inner rod 5 has been fully inserted into the support tube 2 and has pushed the gastric band 20 from the distal end of the support tube 5. Once the gastric band 20 has been deployed, the gastric band 20 can be removed from the inner rod 5.

In use, the gastric band introduction device, in an unactuated state, is inserted into a trocar placed in the patient's abdomen. The device is then actuated by sliding and inserting the inner rod fully into the support tube, thereby deploying the gastric band. The gastric band is then removed from the inner rod by the dissector to be placed around the stomach. Once the gastric band has been removed, the inner rod is pulled back out of the support tube, and the device removed from the trocar.

While the present invention has been illustrated by the description of several embodiments and while the illustrative embodiments have been described in considerable detail, it is not the intention of the applicant to restrict or in any way limit the scope of the appended claims to such detail. Additional advantages and modifications may readily appear to those skilled in the art.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

What is claimed is:

1. A surgical system, comprising:
    a surgical instrument, comprising:
        an elongated support tube having a proximal end, a distal end and an inner surface having a longitudinal groove therein; and
        an elongated inner rod having a proximal end, a distal end and a longitudinal protrusion wherein said inner rod is slidably and coaxially disposed within said support tube wherein said longitudinal protrusion is slidably engaged with said longitudinal groove of said inner surface of said elongated support tube; and
    a gastric band releasably secured to said distal end of said inner rod wherein said distal movement of said rod exposes said gastric band.

2. The surgical system of claim 1 wherein said proximal end of said elongated rod includes a thumb ring.

3. The surgical system of claim 1, wherein said gastric band is releasably secured to said distal end of said elongated inner rod by way of one or more pins.

4. The surgical system of claim 3, wherein said gastric band is releasably secured to said distal end of said elongated inner rod by way of two pins.

5. The surgical system of claim 1, wherein said elongated inner rod further comprises a shelf at said distal end for releasably securing said gastric band.

6. The surgical system of claim 1, wherein said elongated support tube is between about 30 mm and about 50 mm in length.

7. The surgical system of claim 1, wherein said elongated support tube in between about 10 mm and about 20 mm in diameter.

8. The surgical system of claim 7, wherein said elongated support tube is between about 12 mm and about 15 mm in diameter.

9. The surgical system of claim 7, wherein said proximal end of said elongated support tube includes a handle.

10. A method for implanting a gastric band into a patient, comprising the steps of:
    (a) providing a surgical instrument for deploying an adjustable gastric band having:
        (i) an elongated support tube having a proximal end and a distal end;
        (ii) an elongated inner rod slidably and coaxial disposed within said support tube having:
            (1) a proximal end;
            (2) a distal end comprising a shelf having one or more pins located thereon;
        (iii) a gastric band releasably secured to said one or more pins of said shelf of distal end of said inner rod wherein said distal movement of said inner rod exposes said gastric band;
    (b) providing a trocar;
    (c) inserting the trocar into the abdomen of the patient;
    (d) inserting the distal end of the support tube into the trocar;
    (e) distally moving the inner rod of the surgical instrument thereby exposing the gastric band within the abdomen of the patient;
    (f) removing the gastric band from the inner rod of the surgical instrument;
    (g) proximally moving said inner rod of the surgical instrument;
    (h) removing the support tube from the trocar.

11. A surgical instrument for deploying an adjustable gastric band comprising:
    an elongated support tube having a proximal end and an open distal end sized to encompass a gastric band, said elongated support tube further comprising an inner surface having a longitudinal groove therein; and
    an elongated inner rod having a proximal end and a distal end wherein said distal end comprises a shelf for supporting a gastric band, said shelf having one or more pins disposed thereon for releasably engaging a gastric band, said elongated inner rod further comprising a longitudinal protrusion;
    wherein said inner rod is slidably and coaxially disposed within said support tube wherein said longitudinal protrusion of said elongated inner rod is slidably engaged with said longitudinal groove of said inner surface of said elongated support tube, said rod being slidable from a proximal position, wherein said shelf is retained in said elongated support tube, to a distal position, wherein said rod exposes at least a portion of said shelf.

12. The surgical instrument of claim 11 wherein said proximal end of said elongated rod includes a thumb ring.

13. A surgical system, comprising:
    a surgical instrument, comprising:
        an elongated support tube having a proximal end and a distal end, said elongated support tube further comprising an inner surface having a longitudinal groove therein; and
        an elongated inner rod having a proximal end, a distal end and a shelf at said distal end for releasably securing a gastric band, said elongated inner rod further comprising a longitudinal protrusion, wherein said inner rod is slidably and coaxially disposed within said support tube wherein said longitudinal protrusion of said elongated inner rod is slidably engaged with said longitudinal groove of said inner surface of said elongated support tube; and
    a gastric band releasably secured to said shelf of said inner rod wherein said distal movement of said rod exposes said gastric band.

14. The surgical system of claim 13 wherein said proximal end of said elongated rod includes a thumb ring.

15. The surgical system of claim 13, wherein said gastric band is releasably secured to said distal end of said elongated inner rod by way of one or more pins.

16. The surgical system of claim 15, wherein said gastric band is releasably secured to said distal end of said elongated inner rod by way of two pins.

17. A surgical system, comprising:
    an adjustable gastric band; and
    a surgical instrument, comprising:

an elongated support tube having a proximal end and an open distal end sized to encompass the adjustable gastric band; and an elongated inner rod having a proximal end and a distal end wherein said distal end comprises a mechanism releasably engaged to the adjustable gastric band;

wherein said inner rod is slidably and coaxially disposed within said support tube, said rod being slidable from a proximal position, wherein said mechanism retains the adjustable gastric band in the elongated support tube, to a distal position, wherein said rod exposes said mechanism and at least a portion of the adjustable gastric band.

18. A surgical system, comprising:

an adjustable gastric band comprising a trailing conduit; and a surgical instrument, comprising:

an elongated support tube sized to encompass said trailing conduit of said adjustable gastric band, said elongated support tube also having a proximal end and an open distal end sized to encompass said adjustable gastric band; and an elongated inner rod having a proximal end and a distal end, said adjustable gastric band releasably secured to said distal end;

wherein said inner rod is slidably disposed within said support tube, said rod being slidable from a proximal position, wherein said adjustable gastric band is retained in said elongated support tube, to a distal position, wherein said rod exposes at least a portion of said adjustable gastric band.

19. A surgical instrument for deploying an adjustable gastric band comprising:

an elongated support tube having a proximal end, a distal end and an inner surface having a longitudinal groove therein; and an elongated inner rod having a proximal end, a distal end and a longitudinal protrusion, wherein said distal end comprises a shelf for supporting a gastric band, said shelf having one or more pins disposed thereon for releasably engaging a gastric band;

wherein said inner rod is slidably and coaxially disposed within said support tube wherein said longitudinal protrusion of said elongated inner rod is slidably engaged with said longitudinal groove of said inner surface of said elongated support tube and wherein said distal movement of said rod exposes said shelf.

20. A surgical system, comprising:

an unencircled adjustable gastric band; and a surgical instrument, comprising:

an elongated support tube having a proximal end and an open distal end sized to encompass said unencircled adjustable gastric band; and an elongated inner rod having a proximal end and a distal end, said unencircled adjustable gastric band releasably secured to said distal end;

wherein said inner rod is slidably disposed within said support tube, said rod being slidable from a proximal position, wherein said adjustable gastric band is retained in said elongated support tube, to a distal position, wherein said rod exposes at least a portion of said adjustable gastric band.

* * * * *